United States Patent [19]
Hsu et al.

[11] Patent Number: 5,019,671
[45] Date of Patent: May 28, 1991

[54] LIQUID PHASE ISOMERIZATION OF ALKANES

[75] Inventors: Chao-Yang Hsu; Vasant K. Patel, both of Media; David H. Vahlsing, Wynnewood, all of Pa.; James T. Wei, Ridgewood, N.J.; Harry K. Myers, Jr., Cochranville, Pa.

[73] Assignee: Sun Refining and Marketing Company, Philadelphia, Pa.

[21] Appl. No.: 378,334

[22] Filed: Jul. 10, 1989

[51] Int. Cl.$^5$ ................................................ C07C 5/13
[52] U.S. Cl. ..................................... 585/751; 585/750
[58] Field of Search ................................ 585/750, 751

[56] References Cited

U.S. PATENT DOCUMENTS

| | | | |
|---|---|---|---|
| 4,025,418 | 5/1977 | Antos | 585/751 |
| 4,082,651 | 4/1978 | Antos | 585/751 |
| 4,183,805 | 1/1980 | Antos | 585/750 |
| 4,197,188 | 4/1980 | Antos | 585/743 |
| 4,827,076 | 5/1989 | Kokayeff et al. | 585/739 |

Primary Examiner—Curtis R. Davis
Attorney, Agent, or Firm—Donald R. Johnson; Q. Todd Dickinson

[57] ABSTRACT

A sulfated calcined solid catalyst which comprises (1) oxide or hydroxide of Group III or Group IV, e.g. zirconium, metal, (2) oxide or hydroxide of Group V, Group VI or Group VII, e.g. manganese or molybdenum, metal and (3) oxide or hydroxide of Group VIII, e.g. iron, or cobalt metal, is used to isomerize normal alkanes having 4 to 7 carbon atoms per molecule in the liquid phase to obtain high octane number blending components for motor fuel and/or valuable chemical and fuel intermediates.

11 Claims, No Drawings

LIQUID PHASE ISOMERIZATION OF ALKANES

This invention relates to isomerization of $C_4$ to $C_7$ acyclic hydrocarbons.

About 90% of the total butane consumption in the United States is in gasoline manufacture where n-butane is used directly as a blending component, and isobutane is either used for the production of high octane alkylate or for the production of isobutylene to make methyl tert-butyl ether. Chemical uses account for another 6-8% of the total butanes. Due to the recent increased demand for high octane gasoline and the federally regulated reduction of gasoline vapor pressure, there is the need to have a process that can effectively convert normal butane to isobutane to ultimately increase the production of high octane blending components.

Current butane isomerization processes, using either aluminum chloride or chlorinated platinum on alumina or zeolite catalysts, require high operating temperature and use hydrogen as a cracking suppresser. Thus, the commercial processes could only operate in the vapor phase. We have discovered a liquid phase process for the isomerization of normal butane to isobutane. The liquid phase operation provides engineering design and operating cost advantages over conventional vapor phase processes. In the process design area, savings are available due to reduced size of liquid containing lines, reduction of pump energy requirements and elimination of the compressors needed in a vapor phase process to overcome pressure drop through the process, and use of lower cost equipment for heat input by avoiding vaporization of the butane feed. These equipment simplifications also result in less utility requirement for the drivers for pumps and compressors, and eliminate the need of fired heat for vaporization and of cooling water for condensing. In addition, the liquid phase operation also provides other benefits such as lower catalyst deactivation rates than those in the vapor phase operations.

Pentane isomerization is also of commercial interest and is presently carried out with similar platinum on zeolite catalyst and in the vapor phase. The design and cost advantages for a liquid phase pentane isomerization are similar to those described above for butane liquid phase isomerization. $C_6$ and $C_7$ alkanes may also be isomerized according to this invention.

The possibility of liquid phase alkane isomerization is enhanced by the recent discovery of a very active solid superacid catalyst system which is disclosed and claimed in pending application of Hollstein, Wei and Hsu, Ser. No. 247,225 filed Sept. 21, 1988, now U.S. Pat. No. 4,918,041.

The catalyst used in the process according to the invention comprises a sulfated and calcined solid mixture of (1) oxide or hydroxide of metal from a first class consisting of Group III and Group IV, (2) oxide or hydroxide from a second class consisting of Group V, Group VI or Group VII metal and (3) oxide or hydroxide of Group VIII metal. The weight ratio of metal from the second class to Group VIII metal is in the range from 0.1:1 to 2.0:1, preferably 0.2:1 to 1.0:1. The catalyst preferably contains a major amount of oxide or hydroxide of metal from the first class and a minor amount, preferably in the range from 0.02 to 15.0 weight percent, more preferably 0.1 to 4.5 weight percent, of total metal from the second class and Group VIII metal.

The carrier or support for the catalyst according to the invention is an oxide or hydroxide of a Group III or Group IV element. Examples of such suitable elements are aluminum, gallium, indium, thallium, titanium, zirconium, hafnium, silicon, germanium, tin and lead. Preferred are silicon, aluminum, zirconium and mixtures of two or more thereof.

Metals from Groups V, VI or VII which can be used according to the invention include arsenic, antimony, bismuth, vanadium, niobium, tantalum, selenium, tellurium, chromium, molybdenum, tungsten, manganese and rhenium and mixtures of two or more thereof.

Metals from Group VIII which can be used according to the invention include iron, cobalt, nickel, ruthenium, rhodium, palladium, osmium, iridium and platinum and mixtures of two or more thereof.

The catalysts according to the invention may be prepared for example by impregnating a support of a Group III or Group IV metal oxide or hydroxide with an aqueous solution containing compounds of Group VII and Group VIII metals. Alternatively, the support can be impregnated separately with a solution of a Group VII metal compound and a solution of a Group VIII metal compound.

The catalysts according to the invention may also be prepared by co-precipitation of solid hydroxides of (1) Group III or Group IV metals, (2) Group V, Group VI or Group VII metals and (3) Group VIII metals, from aqueous solutions containing compounds of such metals. In such method, the amount of the Group VIII metal hydroxide is typically in the range from 0.01 to 10.0 percent by weight of the total precipitated hydroxide. Mixtures of Group III and Group IV metal oxides or hydroxides, or of two or more from among Group V, Group VI and Group VII metal oxides or hydroxides, may be employed.

Solutions of metal compounds which can be used in the preparation of catalysts according to the invention, by impregnation or co-precipitation, are known in the art. For example, aqueous solution of chloroplatinic acid or tetra-ammine-platinum complex can be used to incorporate platinum in the catalyst. Nitrates of iron and of manganese can be used for example to incorporate those metals in the catalyst. Solutions of zirconium oxychloride or of zirconyl nitrate can be used, for example, to prepare a zirconium support for the catalyst according to the invention. Various other solutions can be employed as needed.

Sulfate ion may be supplied to the catalyst according to the invention by treatment of the solid catalyst with sulfuric acid, for example 0.01-10 N sulfuric acid, preferably 0.1-5 N sulfuric acid. Other compounds such as ammonium sulfate capable of providing sulfate ion can be employed. Compounds such as hydrogen sulfide or sulfur dioxide or mercaptans, capable of forming sulfate ions upon calcining, can also be employed. Preferred catalysts for use according to the invention are those which have been sulfated with ammonium sulfate.

The catalysts according to the invention contain substantial amounts of sulfate ion, preferably in amount of 0.5 to 20 weight percent based on total catalyst, and more preferably 5 to 15 weight percent.

The catalysts according to the invention are calcined at a temperature which is preferably in the range from 450°-800° C., more preferably 550°-700° C., and for a period of time in the range from 30 minutes to 30 hours. Combinations of temperature and time can be chosen in order to provide a desired degree of conversion. For example calcining at 550° C. for 12 hours provides about the same initial conversion of n-butane to isobutane as calcining at 575° C. for 4 hours.

The process according to the invention is used to isomerize normal alkanes having four to seven carbon atoms, namely butane, pentane, hexane and heptane, to convert the straight chain hydrocarbons into branched chain hydrocarbons having higher octane number for use as motor fuel or, as in the case of butane, having enhanced value as an intermediate for such products as tertiarybutyl alcohol and high octane alkylates.

The isomerization is carried out by contacting the hydrocarbon feed in liquid phase with the solid catalyst at temperatures in the range from 0° C. to 250° C., preferably in the range from 20° to 175° C. and at pressure in the range from 1 to 75 atmospheres, more preferably 10 to 50 atmospheres. The isomerization may be conducted either in the presence or absence of hydrogen. If conducted in the presence of hydrogen, the mole ratio of hydrogen to hydrocarbon is preferably in the range from 0.1:1 to 10:1. Inert gas such as nitrogen, helium or argon may be employed. Preferably, the isomerization is conducted in the absence of added gas. If added gas is employed, the amounts added are sufficiently small to avoid vaporization of the liquid hydrocarbon feed. Generally, a temperature is used in the isomerization which is sufficiently high to obtain a desired rate of reaction, but not so high as to result in vaporization and consequently more rapid deactivation of catalyst.

The following examples illustrate the invention:

EXAMPLE 1

Liquid phase isomerization of n-butane in a Parr 300 ml. constant stirring reactor was conducted by charging 2.5 g of catalyst and 50 g of n-butane, and under the reaction conditions of 200 psig and 50° C. The reaction was monitored by taking liquid samples hourly and subjected to GC analyses. The results are shown in Table I.

EXAMPLE 2

Similar reaction procedures and conditions as described in Example 1 were used for this reaction excepting that the amount of catalyst was increased to 5.0 g. The results are shown in Table II.

EXAMPLE 3

A mixed feed of n-butane and nitrogen at a molar ratio of 2:1 was flowed downward through a fixed bed reactor containing 5.0 ml. of catalyst. The reaction conditions were 50° C. and 293 psig. Butane vapor pressure at 50° C. is 57.3 psig, and vapor pressure calculations indicate that this is a liquid phase reaction. GC analyses of the reaction products indicated that the yield of i-butane was 11% when LHSV (liquid hourly space velocity)=0.44 and i-butane yield was 5.1% when LHSV=0.88. The results are shown in Table III.

EXAMPLE 4

Liquid n-butane was pumped upward at a rate of 50 ml. per hour through a fixed bed reactor contining 50 ml. of catalyst and under 220 psig pressure. The reactor temperature was slowly increased to 75° C. and the reaction was run at this temperature for about 70 hours. The reaction samples were taken for on-line GC analyses every hour. The GC results as shown in Table IV indicate that this reaction gives an average of 35% yield of i-butane at 75° C.

EXAMPLE 5

For the purpose of comparison, the same catalyst and reaction conditions as described in Example 4 were used excepting that the reaction pressure was reduced to 50 psig to keep the reaction in the vapor phase. The results obtained from GC analyses as shown in Table V indicated that the vapor phase reaction gave an average of 20% yield of i-butane.

EXAMPLE 6

Liquid phase isomerization of n-pentane to i-pentane was demonstrated using an up-flow reactor and under the conditions of 92 psig and LHSV=1.2. The results are shown in Table VI.

TABLE I

| Liquid Phase Isomerization of n-Butane in a Constant Stirring Reactor | | | | |
|---|---|---|---|---|
| Products(mmol) | 1.0 Hr | 2.0 Hr | 3.0 Hr | 4.0 Hr |
| $C_2$ | 0.01 | 0.01 | 0.01 | 0 |
| $C_3$ | 1.00 | 0.87 | 0.94 | 0.95 |
| $i-C_4$ | 4.92 | 5.69 | 6.00 | 6.42 |
| $i-C_5$ | 0.73 | 0.80 | 0.78 | 0.80 |
| $n-C_5$ | 0.04 | 0.06 | 0.06 | 0.06 |
| $C_5+$ | 0.13 | 0.36 | 0.25 | 0.25 |
| Total (mmol) | 6.83 | 7.79 | 8.04 | 8.48 |
| Mmol/hr/g-Cat | | | | |
| Total Prod. | 2.72 | 1.56 | 1.07 | 0.85 |
| $i-C_4$ | 0.38 | 1.14 | 0.80 | 0.64 |
| Sel.(% $i-C_4$) | 66.3 | 68.1 | 69.6 | 70.5 |

TABLE II

| Liquid Phase Isomerization of n-Butane in a Constant Stirring Reactor | | | | |
|---|---|---|---|---|
| Products(mmol) | 1.0 Hr | 2.0 Hr | 3.0 Hr | 4.0 Hr |
| $C_2$ | 0.02 | 0.02 | 0.01 | 0.01 |
| $C_3$ | 1.12 | 1.30 | 1.06 | 1.10 |
| $i-C_4$ | 8.49 | 10.1 | 11.3 | 11.8 |
| $i-C_5$ | 0.84 | 0.83 | 0.90 | 0.89 |
| $n-C_5$ | 0.09 | 0.10 | 0.10 | 0.11 |
| $C_5+$ | 0.10 | 0.18 | 0.21 | 0.24 |
| Total (mmol) | 10.66 | 12.54 | 13.54 | 14.17 |
| Mmol/hr/g-Cat | | | | |
| Total Prod. | 2.13 | 1.26 | 0.90 | 0.71 |
| $i-C_4$ | 1.70 | 1.01 | 0.75 | 0.59 |
| Sel.(% $i-C_4$) | 75.6 | 76.5 | 79.7 | 80.7 |

TABLE III

| Liquid Phase Isomerization of n-Butane in a Fixed Bed Down Flow Reactor (Reaction conditions: 50° C., 293 psig.) (Feed composition: butane/nitrogen = 2/1) | | | | | | | | |
|---|---|---|---|---|---|---|---|---|
| | Reaction Time (hr) | | | | | | | |
| GC analyses | 14.0 | 16.0 | 18.0 | 20.0 | 23.0 | 24.0 | 25.0 | 26.0 |
| | LHSV (1/Hr) | | | | | | | |
| (Weight %) | 0.44 | 0.44 | 0.44 | 0.44 | 0.88 | 0.88 | 0.88 | 0.88 |
| $C_3$ | 0.136 | 0.090 | 0.134 | 0.133 | 0.036 | 0.030 | 0.032 | 0.028 |
| $i-C_4$ | 12.28 | 11.78 | 13.01 | 11.76 | 5.670 | 5.407 | 5.125 | 4.128 |
| $n-C_4$ | 87.46 | 88.06 | 86.79 | 88.02 | 91.36 | 94.45 | 94.57 | 91.96 |
| $i-C_5$ | 0.103 | 0.010 | 0.011 | 0.080 | 2.302 | 0.103 | 0.263 | 2.348 |
| $n-C_5$ | 0.020 | 0.010 | 0.011 | 0.011 | 0.623 | 0.004 | 0.003 | 0.935 |

TABLE IV

| Liquid Phase Isomerization of Butane Using an Up Flow Fixed Reactor at Various Temperatures (Pressure: 1235-150 psig., LHSV = 1.0) | | | | | | | |
|---|---|---|---|---|---|---|---|
| Reaction Time (Hr) | | | | | | | |
| 10 | 15 | 20 | 25 | 30 | 35 | 40 | 45 |
| Reaction Temp.(°C.) | | | | | | | |

TABLE IV-continued

Liquid Phase Isomerization of Butane
Using an Up Flow Fixed Reactor at Various Temperatures
(Pressure: 1235-150 psig., LHSV = 1.0)

| GC Analyses | Reaction Press.(Psig) | | | | | | | |
|---|---|---|---|---|---|---|---|---|
| | 50 | 50 | 50 | 60 | 60 | 60 | 60 | 60 |
| (Weight %) | 100 | 100 | 100 | 130 | 135 | 135 | 135 | 135 |
| $C_3$ | 0.45 | 0.44 | 0.41 | 0.55 | 0.56 | 0.56 | 0.55 | 0.54 |
| $i$-$C_4$ | 18.30 | 17.59 | 16.09 | 23.16 | 23.95 | 22.92 | 22.09 | 21.51 |
| $n$-$C_4$ | 80.84 | 81.63 | 83.20 | 75.79 | 74.95 | 76.03 | 76.89 | 77.49 |
| $i$-$C_5$ | 0.33 | 0.28 | 0.25 | 0.41 | 0.44 | 0.40 | 0.39 | 0.37 |
| $n$-$C_5$ | 0.06 | 0.05 | 0.05 | 0.08 | 0.09 | 0.08 | 0.08 | 0.07 |

| | Reaction Time (Hr) | | | | | | | |
|---|---|---|---|---|---|---|---|---|
| | 50 | 55 | 60 | 70 | 80 | 90 | 100 | 140 |
| | Reaction Temp.(°C.) | | | | | | | |
| | 65 | 70 | 70 | 70 | 74 | 76 | 76 | 76 |
| GC Analyses | Reaction Press.(Psig) | | | | | | | |
| (Weight %) | 135 | 135 | 128 | 128 | 150 | 150 | 150 | 150 |
| $C_3$ | 0.70 | 0.67 | 0.90 | 0.91 | 1.17 | 1.11 | 1.08 | 0.99 |
| $i$-$C_4$ | 27.63 | 26.87 | 33.83 | 32.71 | 39.17 | 38.34 | 37.74 | 35.92 |
| $n$-$C_4$ | 70.99 | 71.79 | 64.26 | 65.47 | 57.50 | 58.45 | 58.92 | 61.93 |
| $i$-$C_5$ | 0.55 | 0.54 | 0.81 | 0.73 | 1.09 | 1.07 | 1.02 | 0.93 |
| $n$-$C_5$ | 0.11 | 0.11 | 0.17 | 0.15 | 0.23 | 0.23 | 0.23 | 0.20 |

TABLE V

Vapor Phase Isomerization of Butane
Using a Fixed Bed Reactor at Various Temperatures

| | Reaction Time (Hr) | | | | | | | |
|---|---|---|---|---|---|---|---|---|
| | 15 | 25 | 35 | 45 | 56 | 66 | 76 | 86 |
| | Reaction Temp.(°C.) | | | | | | | |
| | 75 | 75 | 85 | 85 | 85 | 85 | 85 | 85 |
| GC Analyses | Reaction Press.(Psig) | | | | | | | |
| (Weight %) | 100 | 100 | 100 | 100 | 100 | 100 | 100 | 100 |
| $C_3$ | 0.43 | 0.46 | 0.77 | 0.68 | 0.61 | 0.57 | 0.54 | 0.49 |
| $i$-$C_4$ | 17.08 | 16.03 | 28.22 | 25.16 | 22.56 | 20.84 | 19.58 | 18.18 |
| $n$-$C_4$ | 82.04 | 83.16 | 70.15 | 73.50 | 76.22 | 78.06 | 80.86 | 68.35 |
| $i$-$C_5$ | 0.37 | 0.29 | 0.70 | 0.53 | 0.49 | 0.44 | 0.40 | 0.38 |
| $n$-$C_5$ | 0.07 | 0.06 | 0.13 | 0.10 | 0.09 | 0.08 | 0.07 | 0.07 |

TABLE VI

Liquid Phase Isomerization of n-Pentane
In an Up Flow Fixed Bed Reactor at Various Temperatures
(Reaction conditions: Press. = 92 psig., LHSV - 1.2)

| | Reaction Time (Min) | | | | | | | | | | |
|---|---|---|---|---|---|---|---|---|---|---|---|
| | 37 | 67 | 97 | 127 | 157 | 187 | 217 | 247 | 277 | 307 | 337 |
| GC Analyses | Reaction Temp.(°C.) | | | | | | | | | | |
| (Weight %) | 19 | 19 | 20 | 28 | 36 | 44 | 52 | 60 | 68 | 74 | 75 |
| $i$-$C_4$ | 0.07 | 0.23 | 0.35 | 0.28 | 0.27 | 0.44 | 0.73 | 1.64 | 1.70 | 2.76 | 2.21 |
| $i$-$C_5$ | 5.70 | 9.95 | 12.04 | 12.12 | 13.22 | 18.35 | 23.7 | 29.32 | 20.44 | 35.04 | 35.22 |
| $n$-$C_5$ | 93.80 | 89.20 | 86.80 | 86.90 | 85.60 | 78.98 | 73.96 | 66.66 | 65.28 | 57.82 | 59.16 |
| 2,2-$DMC_4$ | 0.03 | 0.08 | 0.11 | 0.09 | 0.09 | 0.13 | 0.20 | 0.39 | 0.39 | 0.55 | 0.44 |
| 2,3-$DMC_4$ | 0.01 | 0.01 | 0.01 | 0.01 | 0.02 | 0.02 | 0.05 | 0.11 | 0.14 | 0.24 | 0.21 |
| 2-$MC_5$ | 0.04 | 0.13 | 0.21 | 0.17 | 0.19 | 0.28 | 0.45 | 0.94 | 1.03 | 1.60 | 1.45 |
| 3-$MC_5$ | 0.03 | 0.06 | 0.09 | 0.08 | 0.09 | 0.13 | 0.20 | 0.41 | 0.46 | 0.71 | 0.64 |
| $n$-$C_6$ | 0.01 | 0.01 | 0.02 | 0.01 | 0.02 | 0.03 | 0.05 | 0.11 | 0.12 | 0.20 | 0.18 |

The invention claimed is:

1. Method of isomerizing a feedstock comprising acyclic hydrocarbons having 4 to 7 carbon atoms per molecule which comprises contacting said feedstock in liquid phase with a catalyst comprising a sulfated and calcined solid mixture of (1) oxide or hydroxide of element from a first class consisting of Group III or Group IV elements, (2) oxide or hydroxide of metal from a second class consisting of Group V, Group VI or Group VII metals, and (3) oxide or hydroxide of Group VIII metal, the ratio of metal from said second class to Group VIII metal being in the range from 0.1:1 to 2.0:1, at a temperature in the range from 0 to 250° C., and a pressure in the range from 1 to 75 atmospheres.

2. Method according to claim 1 wherein the catalyst contains, from said first class, silicon, aluminum, zirconium, or mixtures comprising two or more thereof.

3. Method according to claim 2 wherein said element from said first class is zirconium.

4. Method according to claim 1 wherein said metal is iron.

5. Method according to claim 1 wherein said metal is cobalt.

6. Method according to claim 1 wherein said metal from said second class is manganese, rhenium, chromium, molybdenum, tungsten, vanadium, niobium, arsenic, antimony or bismuth or mixtures comprising two or more thereof.

7. Method according to claim 6 wherein said metal is manganese.

8. Method according to claim 6 wherein said metal is molybdenum.

9. Method according to claim 1 wherein said catalyst has been sulfated with ammonium sulfate.

10. Method according to claim 1 wherein said catalyst contains 5 to 15 weight percent of sulfate ion.

11. Method according to claim 1 wherein the contacting is in the absence of added gas.

* * * * *